Dec. 3, 1968 G. D. SITTON, SR Plant Pat. 2,847
ROSE PLANT
Filed Dec. 16, 1966
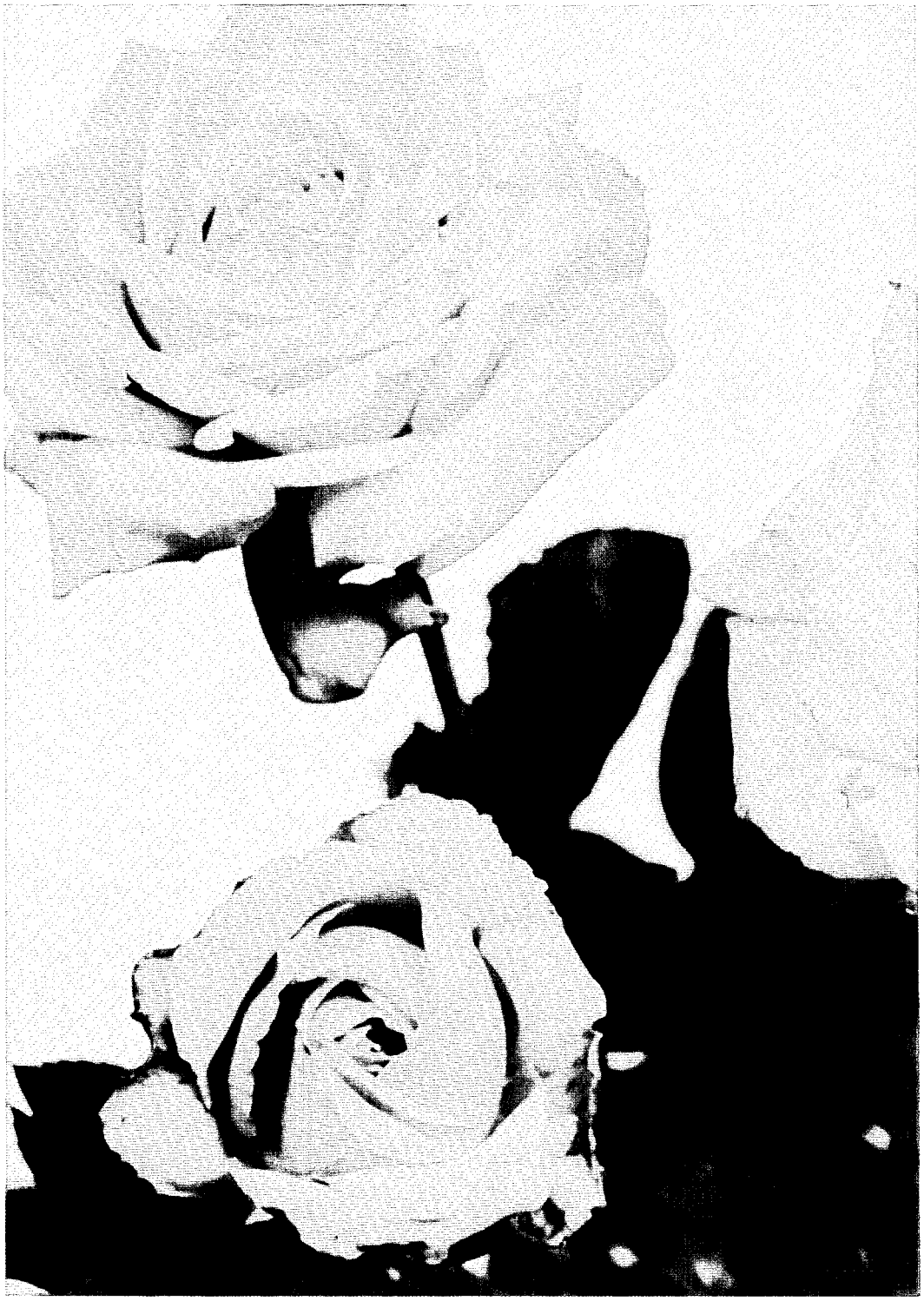

United States Patent Office

Plant Pat. 2,847
Patented Dec. 3, 1968

2,847
ROSE PLANT
George D. Sitton, Sr., Rte. 3, Box 29,
Lindale, Tex. 75771
Filed Dec. 16, 1966, Ser. No. 602,429
1 Claim. (Cl. Plt.—20)

The present invention relates to a new and distinct variety of rose plant of the hybrid tea class which was discovered by me as a sport of the variety known as "The Alamo" (Plant Patent No. 1,689).

I discovered the new variety in one of my cultivated fields near Hopewell Community about ten miles north of Tyler, Tex. I found this mutation or change from the normal appearance in my field production of "The Alamo" variety, with the prominent difference being the orange red color instead of the usual red that "The Alamo" variety has. This first observation was made in 1959, and since then I have propagated from 30 to 40 plants to see if the new variety would remain true to the original that was found. It has remained true each year and is ready for additional increase for its first introduction. The unique color is considered to be the only significant difference from the parent type variety.

The following is a detailed description of my new variety, with color terminology in accordance with Nickerson's Color Fan (American Horticultural Council) and the British Horticultural Color Chart, except where general color terms of ordinary dictionary significance are obvious:

Type: Hardy; bush; outdoor; sport; for garden decoration.
Class: Hybrid tea.
Parentage: Sport of "The Alamo."
Propagation: Holds its distinguishing characteristics through succeeding propagations by budding.

*Flower*

Locality where grown and observed: Near Tyler, Tex.
Continuity: Continuous through growing season.
Fragrance: Mild, tea.
Flowers borne: Singly usually, but sometimes in clusters of three, on fairly strong stems that are longer than for most hybrid tea roses.
Quality of bloom: Free, outdoors.
Bud:
*Peduncle.*—Medium length; medium caliper for single stem flowers but somewhat smaller caliper for cluster flowers; stiff peduncle even with smaller caliper; mostly smooth but a few prickles. Color—medium green.

*Before calyx breaks.*—Size—medium. Form—same as "The Alamo." Color—Dark Red 5R 3/7 to Moderate Reddish-Brown 7.5R 3/6.
*As calyx breaks.*—Color—Moderate Reddish-Brown 7.5R 3/6.
*As first petals open.*—Size—medium. Form—same as "The Alamo." Color outside—Strong Red 5R 4/12; Vivid Red 5R 5/13.
*Opening.*—Opens well and is long lasting with much substance, the same as the parent.
Bloom:
*Size.*—Same as "The Alamo."
*Petalage.*—Same as "The Alamo."
*Form.*—Same as "The Alamo."
Petals:
*Texture.*—Same as "The Alamo."
*Shape.*—Same as "The Alamo."

This description of a newly opened flower was made from a rose grown in the month of October near Tyler, Tex.
*Color.*—Signal Red 719 as petals open, changing to Scarlet 19/1 with a silvery sheen as the blossom matures (Horticultural Color Chart). Inner petals; the same as outer.
*General color effect.*—A dark color when opening and fading slightly when fully open. Petals hold to receptacle even when old, with very little shedding of petals.
*Flower longevity.*—Same as for "The Alamo," sometimes lasting in desirable color for more than a week even in the summer months.

*Reproductive organs*

Same as for "The Alamo."

*Plant*

Same as for "The Alamo."

The accompanying drawing shows typical specimens of the blooms and foliage of my new variety as depicted in color as nearly true as it is reasonably possible to make the same in a color illustration of this character.

I claim:

1. A new and distinct variety of rose plant of the hybrid tea class, substantially as herein shown and described, characterized particularly as to novelty by the unique color.

No references cited.

ROBERT E. BAGWILL, *Primary Examiner.*